United States Patent [19]

Fisher et al.

[11] Patent Number: 5,328,821

[45] Date of Patent: Jul. 12, 1994

[54] COLD AND CRYO-PRESERVATION METHODS FOR HUMAN TISSUE SLICES

[76] Inventors: Robyn Fisher, 15555 N. Oracle Rd., Tucson, Ariz. 85737; Klaus Brendel, 3231 N. Manor Dr., Tucson, Ariz. 85715

[21] Appl. No.: 806,047

[22] Filed: Dec. 12, 1991

[51] Int. Cl.$^5$ .................... A01N 1/02; C12N 5/00; C12N 1/04

[52] U.S. Cl. .................... 435/1; 435/2; 435/240.1; 435/260

[58] Field of Search .......... 435/1, 2, 240.1, 260

[56] References Cited

U.S. PATENT DOCUMENTS

| | | | |
|---|---|---|---|
| 3,431,172 | 3/1969 | Rajamannan | 435/1 |
| 3,458,397 | 7/1969 | Myers et al. | 435/1 |
| 3,551,290 | 12/1970 | Kuwahara | 435/1 |
| 3,676,298 | 7/1972 | Moczar et al. | 435/1 |
| 3,682,776 | 8/1972 | Grandmann et al. | 435/1 |
| 3,753,357 | 8/1973 | Schwartz | 435/1 |
| 3,766,015 | 10/1973 | Dardas | 435/1 |
| 3,881,990 | 5/1975 | Burton et al. | 435/1 |
| 3,892,628 | 7/1975 | Thorne et al. | 435/1 |
| 3,912,809 | 10/1975 | Rendon | 435/1 |
| 3,914,954 | 10/1975 | Doerig | 435/1 |
| 3,935,065 | 1/1976 | Doerig | 435/1 |
| 3,936,269 | 2/1976 | Bayne | 435/1 |
| 3,943,993 | 3/1976 | Smith | 435/1 |
| 3,983,712 | 10/1976 | Söder et al. | 435/1 |
| 4,004,975 | 1/1977 | Lionetti et al. | 435/1 |
| 4,008,754 | 2/1977 | Kraushaar et al. | 435/1 |
| 4,018,911 | 4/1977 | Lionetti et al. | 435/1 |
| 4,030,314 | 6/1977 | Strehler et al. | 435/1 |
| 4,040,785 | 8/1977 | Kim et al. | 435/1 |
| 4,107,937 | 8/1978 | Chmiel | 435/1 |
| 4,117,881 | 10/1978 | Williams et al. | 435/1 |
| 4,155,331 | 5/1979 | Lawrence et al. | 435/1 |
| 4,353,930 | 10/1982 | Hirahara | 435/1 |
| 4,471,629 | 9/1984 | Toledo-Pereyra | 435/1 |
| 4,473,552 | 9/1984 | Jost | 435/1 |
| 4,473,637 | 9/1984 | Gulbert | 435/1 |
| 4,494,385 | 1/1985 | Kuraoka et al. | 435/1 |
| 4,559,298 | 12/1985 | Fahy | 435/1 |
| 4,565,643 | 1/1986 | Arai | 435/1 |
| 4,601,909 | 7/1986 | Nagoshi | 935/1 |
| 4,609,622 | 9/1986 | Koha et al. | 435/29 |
| 4,681,839 | 6/1987 | Swartz | 435/1 |
| 4,688,387 | 8/1987 | Conaway | 435/1 |
| 4,695,460 | 9/1987 | Holme | 435/1 |
| 4,695,536 | 9/1987 | Lindstrom et al. | 435/1 |
| 4,727,018 | 2/1988 | Eichner et al. | 435/1 |
| 4,745,759 | 5/1988 | Bauer et al. | 435/1 |
| 4,798,824 | 1/1989 | Belzer et al. | 435/1 |
| 4,799,361 | 1/1989 | Linner | 435/1 |
| 4,812,310 | 3/1989 | Sato et al. | 435/1 |
| 4,832,972 | 5/1989 | Toledo-Flores et al. | 435/1 |
| 4,837,390 | 6/1989 | Reneau | 435/1 |
| 4,840,034 | 6/1989 | Liberman | 435/1 |
| 4,840,035 | 6/1989 | Liberman | 435/1 |
| 4,865,871 | 9/1989 | Livesey et al. | 435/1 |
| 4,873,186 | 10/1989 | Chen et al. | 435/1 |
| 4,879,283 | 11/1989 | Belzer et al. | 435/1 |
| 4,890,457 | 1/1990 | McNally et al. | 435/1 |
| 4,920,044 | 4/1990 | Bretan | 435/1 |
| 4,931,361 | 6/1990 | Baldeschwieler et al. | 435/1 |
| 4,940,599 | 7/1990 | Engler et al. | 435/1 |
| 4,956,272 | 9/1990 | Kakimoto et al. | 435/1 |
| 4,959,319 | 9/1990 | Skelnik et al. | 435/1 |
| 4,965,186 | 10/1990 | Grischenko et al. | 435/1 |
| 4,978,540 | 12/1990 | Lee | 435/1 |
| 4,978,546 | 12/1990 | Haram | 435/1 |
| 4,980,277 | 12/1990 | Junilla | 435/2 |
| 5,145,769 | 9/1992 | McNally et al. | 435/1 |
| 5,145,770 | 9/1992 | Tubo et al. | 435/1 |
| 5,145,771 | 9/1992 | Lemasters et al. | 435/1 |
| 5,158,867 | 10/1992 | McNally et al. | 435/1 |

OTHER PUBLICATIONS

Belzer et al. *Transplantation*. vol. 45. pp. 673–676. 1988.

(List continued on next page.)

*Primary Examiner*—Douglas W. Robinson
*Assistant Examiner*—L. Blaine Lankford
*Attorney, Agent, or Firm*—Dilworth & Barrese

[57] ABSTRACT

Cold-and cryo-preservation solutions for tissue slices include a limited amount of glucose. The solutions provide extended cold storage of the slices without a loss of viability. The solutions also allow cryopreservation of the slices, so that the slices may be stored until needed and then thawed, cultured, packaged and distributed.

7 Claims, No Drawings

OTHER PUBLICATIONS

Metabolism Of Dichlorobenzenes In Organ Cultered Liver Slices, Biological Reactive Intermediates IV (1990), pp. 717–723.

Cryopreservation Of Pig And Human Liver Slices, Cryobiology 28 (1991), pp. 131–142.

Preparation And Utilization Of Positional Renal Slices For In Vivo Nephrotoxicity Studies Charles E. Ruegg et al., pp. 197–230.

Biotransformation Activity In Vitrified Human Liver Slices, Cryobiology 28, (1991) pp. 216–226.

Maintenance Of Adult Rat Liver Slices In Dynamic Organ Culture, In Vitro Cellular & Developmental Biology, vol. 22, No. 12, (Dec. 1986), pp. 706–712.

A Dynamic Liver Culture System: A Tool For Studying Chemical Biotransformation And Toxicity, Mechanisms and Models in Toxicology, Arch. Toxicol. Suppl. 11 (1987) pp. 20–33.

In Vitro Cytotoxicity of Allyl Alcohol And Bromobenzene In A Novel Organ Culture System, Toxcology and Applied Pharmacology (1987), pp. 509–522.

Dynamic Organ Culture Of Precision Liver Slices For In Vitro Toxicology, Life Sciences, vol. 36 (1985), pp. 1367–1375.

N-Acetyl S-(1,2-Dichlorovinyl)-L-Cysteine Produces A Similar Toxicity to S-(1,2-dichlorovinyl)-L-Cysteine In Rabbit Renewal Slices: Differential Transport And Metabolism, Tox. and App. Pharm. 101 (1989), pp. 205–219.

Assessment of S-(1,2-Dichlorovinyl)-L-Cysteine Induced Toxic Events In Rabbit Renewal . . . Chem.-Biol. Interactions, vol. 75 (1990) pp. 153–170.

Tissue Slicing And Culturing Revisited, Current Techniques, vol. 8, (1987), pp. 11–15.

A New Instrument For The Rapid Preparation Of Tissue Slices, Analytical Biochemistry, vol. 104 (1980), pp. 118–123.

Toxicity Of Chlorobenzenes In Cultured Rat Liver Slices, In Vitro Toxicology, vol. 3, No. 2 (1990), pp. 181–194.

Precision Cut Liver Slices: A New In Vitro Tool In Toxicology, No. 4, Smith et al., pp. 93–130.

Principles Of Solid-Organ Preservation By Cold Storage, Du Pont Pharmaceuticals, vol. 45, No. 4, (Apr. 1988), pp. 673–676.

Extended Preservation Of Human Liver Grafts With UW Solution, Du Pont Pharmaceuticals, vol. 261, No. 5, (Feb. 1989), pp. 711–714.

COLD AND CRYO-PRESERVATION METHODS FOR HUMAN TISSUE SLICES

FIELD OF THE INVENTION

The present invention relates generally to methods and solutions for the preservation of tissue. More particularly, this invention relates to solutions for preserving tissue slices in a viable state and cold- and cryo-preservation methods for human tissue slices employing these solutions.

BACKGROUND OF THE INVENTION

Thousands of chemical substances are examined each year for their biotransformation and potential toxicity. Nearly all chemical toxicity tests will be conducted on rats, mice, guinea pigs, rabbits, cats, dogs and monkeys, with the results from these animal experiments being extrapolated to humans. While the reactions of rats, rabbits and mice to chemicals together with metabolite patterns are currently considered acceptable predictors of the toxic effects these substances will have on the human organism, the significance of animal experimentation and subsequent data extrapolation is a questionable science since species variation can be significant. By utilizing human in vitro biotransformation technology, the fate and disposition of potentially toxic, environmental/industrial chemicals or prospective drugs in man can be more accurately determined without exposing living humans or laboratory animals to the actual compounds.

For the past several years, metabolism has been studied using subcellular (microsome) fractions obtained from human livers. Systems such as this are important for metabolite identification and rate of formation. The use of such subcellar fractions only allows one to determine if a particular enzymatic process exists within the fraction and its ability to react with a given compound. However, the observance of a specific enzymatic activity in an isolated subcellular fraction does not mean that this reaction will be expressed to the same extent in vivo. Extensive cellular organization and compartmentalization within the cell determine chemical disposition of a test compound. Thus, it would be optimal to have an in vitro system that retains the tissue's inherent organization and which will best reflect human in vivo biotransformation. An intact in vitro metabolism system would also mimic both the metabolic and chemical reactions that occur during in vivo metabolism.

Intact sections of human tissues appear to maintain crucial characteristics of cellular organization while allowing the researcher the versatility of an in vitro system. This is important since there is a heterogeneous distribution of biotransformation enzymes within the tissue and intact tissue sections sample all of these sites exactly as in the whole organism.

Human livers, kidneys, lungs, hearts and pancreas are harvested from organ donors usually in a hospital or organ bank and made available through a nationwide network the transplant centers. Occasionally, suitable matches can not be found or the prospective recipient develops complications and the tissue then becomes available for research. In order to do certain biological studies such as xenobiotics metabolism, intermediary metabolism, hormone receptor studies or chemical induced toxicity, the tissue has to be fully intact and comparable in its viability to the standards set for transplantable tissue. This optimal viability is particularly important for biochemical and cell biological studies requiring fully functional cells.

Two investigations, Pollard and Dutton, reported limited success using tissue fragments and slices in drug disposition studies, but mentioned two specific problems associated with their methods. The first was their inability to prepare uniform, viable sections rapidly. The second problem centered around the failure to maintain tissue viability throughout the experiment.

In the mid 1980's the first problem encountered by Pollard and Dutton was overcome by the introduction of the Krumdieck et al. tissue slicer to produce non-traumatized, precision-cut liver slices ($\pm 5\%$ variation in thickness) from 60 to 500 microns thick at a rapid rate under physiological conditions.

The problem of maintaining tissue viability during an experiment, however, has not yet been satisfactorily overcome. Inappropriately cultured tissue sections no longer have the gas, fluid and nutrient exchange that exist in vivo. To overcome these deficiencies, an incubation system was developed in which the liver slices were exposed to the gas phase while the side resting on the support was constantly bathed in media. The media was supposed to coat the whole slice by capillary action, and the submerged side receives gas via diffusion. This however, proved inadequate to maintain the slice. The submerged slice rapidly deteriorated and only cells in the gas-tissue interface remained viable. A number of investigators have maintained slices in culture for 12 hours to several days with only the cells at the gas-tissue phase remaining viable.

An organ culture system was developed in an attempt to overcome the inadequate oxygenation of the conventional culture system. This new system combined the advantages of increased surface area for oxygenation and nutrient uptake with those of conventional organ culture (maintain organ architecture). Smith et al. floated slices into cylindrical, stainless steel screen supports fitted with two narrow stainless steel sleeves. The tissue adhered to the screens during culture. The cylinders were then placed inside vials that contain sufficient media to wet the slices when the vials are on their sides. The vials were flushed with 95:5% $O_2:CO_2$, sealed, and incubated on a heated (37° C.) vial rotator. As the vial was rotated the support inside also rotated causing the underside of the tissue to be alternatively exposed to media or gas while the upper side was continuously exposed to gas. This dynamic organ culture system was far superior to conventional systems resulting in a completely viable slice for up to 48 hours. In addition, it has been reported that animal liver slices seemed to improve during culturing, raising the possibility that the human liver slices might actually repair themselves during this type of culturing.

U.S. Pat. No. 4,920,044 to Bretan describes an intracellular flush solution for preserving organs. By way of background, Bretan provides the compositions of four other flush solutions, namely: Collins-2 Flush; Sacks-2 Flush; Belzer perfusate; and UW-1 Flush. Bretan states that D-glucose has been recently shown to exacerbate acute renal ischemia damage in dogs. Mannitol is therefore substituted for glucose in the Bretan solution (Bretan, column 10, lines 32–39).

U.S. Pat. No. 4,798,824 to Belzer et al. describes perfusate for the preservation of organs, particularly kidneys. The Belzer et al. '824 perfusate contains hydroxyethyl starch ("HES") in place of human serum albumin for colloidal osmotic support.

U.S. Pat. No. 4,879,283 to Belzer et al. describes a solution which includes hydroxyethyl starch ("HES") for the preservation of organs. Belzer et al. indicate that glucose, the main impermeant in Collins' solution, is not an effective impermeant for the liver or pancreas and readily enters cells. Thus, Belzer et al. completely remove glucose from their formulation and replace glucose with HES.

Belzer et al. have also reported that preservation solutions containing high concentrations of glucose pose a two-fold disadvantage since glucose is not an effective impermeant to prevent cell swelling and glucose could stimulate acidosis. Belzer et al., *Transplantation*, Vol. 45, pgs. 673–676, (April, 1988).

No prior cold preservation solution known to applicants has been successful in maintaining the viability of tissue for longer than 72 hours.

It is an object of this invention to provide a preservation solution which permits the cold preservation of viable tissue for periods longer than three days, preferably for seven to ten days.

It is a further object of this invention to provide a method of cold preserving tissue for up to ten days while maintaining viability of the tissue and for cryopreserving tissue for extended periods up to three years while maintaining the viability of the tissue.

It is also an object of this invention to expand the availability of human tissue for testing, including xenobiotics metabolism, intermediary metabolism, hormone receptor and chemical induced toxicology testing.

It is a further object of this invention to provide human tissue samples for testing, which tissue samples preserve the cellular organization and compartmentalization within the human tissue sample. It is a further object of the present invention to provide an organ culture system which allows for the accurate determination of in vivo biotransformation with an in vitro system.

It is also an object of this invention to provide a method of freezing and storing viable human tissues. It is a further object of this invention to provide an integrated procedure which includes tissue slicing-cold storage-cryopreservation-special packaging for shipping and later culturing-cold storage during transport and packaging in specified self-righting cold storage containers. All steps may advantageously be performed in one basic solution, which is modified by one additional ingredient (DMSO) for cryopreservation and replacement of some potassium for sodium in the final culturing phase. It is also an object of this invention to provide a preservation method which will allow the establishment of a tissue bank comprised of valuable human tissue slices to be utilized for research.

It is a further object of this invention to reduce the amount of preclinical animal trials by providing a method for the preservation and distribution of viable human tissue slices for testing.

SUMMARY OF THE INVENTION

Preservation solutions in accordance with the present invention contain glucose in an amount sufficient to maintain the metabolic functions of the tissue cells but insufficient to stimulate acidosis and permit the cold preservation of viable tissue for periods longer than 72 hours, normally up to about ten days. The preservation solutions of the present invention are suitable for use in conjunction with a cryoprotectant to provide the cryopreservation of viable tissue for periods of three years or longer.

The present invention also embraces methods of cold preservation comprising the steps of contacting a tissue slice with a preservation solution containing glucose in an amount sufficient to allow the metabolic functions of the tissue cells but insufficient to result in acidosis and storing the slices at about zero degrees centigrade.

In another aspect the present invention embraces a method of cryopreserving tissue slices comprising the steps of: contacting the tissue with a preservation solution containing a) glucose in an amount sufficient to maintain the metabolic functions of the cell but insufficient to cause acidosis and b) a cryoprotectant; and then cryopreserving the tissue by cooling at a controlled rate whereby the viability of the tissue slices is maintained in the cryopreserved state. After a period of months or years, the tissue may be thawed, reconditioned, specifically packaged for dynamic culture, placed in the preservation solution and stored at about zero degrees centigrade.

Tissue slices which have been contacted with the preservation solutions of the present invention may be packaged and shipped in self-righting cold packs in accordance with another aspect of this invention.

DESCRIPTION OF PREFERRED EMBODIMENTS

The preservation solutions of the present invention contain glucose in an amount sufficient to maintain the metabolic function of the cell but an amount insufficient to cause acidosis. The effectiveness of any physiologically acceptable preservation buffer solution may be improved by adjusting the amount of glucose in the solution in accordance with the present invention.

The preservation solutions of this invention may be based upon any physiologically acceptable solution. By the phase "physiologically acceptable" solution it is meant that the solution tends to (1) minimize hypothermic-induced cell swelling; (2) prevent intracellular acidosis; (3) prevent the expansion of extracellular space; (4) prevent injury from oxygen free radicals; and (5) provide substrates for regenerating high energy phosphate compounds.

In general, a physiologically acceptable solution will contain an effective impermeant to prevent or minimize hypothermic induced cell swelling. Impermeants which may be included in the physiologically acceptable solution include, but are not limited to $K^+$-lactobionate, raffinose, hydroxyethyl starch, gluconate ($K^+$ salt), saccharate ($K^+$ salt), mannitol and polyvinylpyrrolidone.

Physiologically acceptable solutions also generally include a hydrogen ion buffer, such as for example, a phosphate. Adenosine, an ATP precursor or other agents which provide precursors for the regeneration of high energy phosphate compounds may also be included in suitable base solutions.

Additionally, the base solution may include substances that create colloidal osmotic pressure and allow the free exchange of constituents of the solution without expanding the interstitial space. Suitable ingredients for these purposes include albumin, polyvinylpyrolidene, polyethylene glycol, dextran, and hydroxyethel starch.

Ingredients or agents which inhibit the generation of $O_2$ free radicals may also be included in the physiologically acceptable base solution used to form the solution. Oxygen free radical generation is believed to be inhibited by allopurinol, an inhibitor of xanthine oxidase as well as mannitol and other radical scavengers and heavy metal complexes such as deferroxamin and EDTA.

Other ingredients which may be included in a physiologically acceptable base solution include, but are not limited to inorganic salts such as KCl, $MgSO_4$, MgCl, $NaHCO_3$, $KHCO_3$, reducing agents such as glutathione, vitamin E, vitamin C, hormones such as dexamethasone, insulin, antibiotics such as penicillin, gentamycin and bactrim or calcium channel blockers such as verapamil.

Suitable preservation solutions may have an osmolality in the range of 300 to 450 and a neutral to slightly basic pH, preferably a pH in the range of 7.4 to 7.6.

Presently known physiologically acceptable solutions upon which the solutions of the present invention may be based include those disclosed in the above mentioned U.S. Pat. Nos. 4,920,044; 4,798,824; and 4,879,783 the disclosures of which are incorporated herein by reference. The compositions of some of the presently known solutions are presented in Table 1. These known solutions may serve as the base for the preservation solutions of the present invention, provided their glucose content is adjusted to an amount which is sufficient to maintain the metabolic functions of the cell but insufficient to cause acidosis within the cell. By adjusting the glucose content of these known solutions their ability to preserve tissue slices can be substantially improved. Use of the preferred solutions of this invention may provide a two to three-fold increase in preservation time over known preservation solutions.

normally be below in the range 500–750 mg per liter. For kidney tissue the amount of glucose should normally be in the range 750 mg–1000 mg/Liter. For lung tissue the amount of glucose used should normally be in the range 300 mg–600 mg/Liter. For heart tissue, 600 mg–900 mg/Liter glucose should normally be used. For pancreas tissue, 300 mg–500 mg/Liter will normally be appropriate.

The amount of glucose present should be an amount sufficient to maintain the metabolic functions of the cell. Any known method may be used to determine if a sufficient amount of glucose is present. For example, one test for determining that glucose is present in an amount sufficient to maintain the metabolic functions of the tissue cells would be to monitor the consumption of glucose and/or the generation of metabolic products of glucose, such as, for example, lactic acid. Experimental protocols to determine the presence of the appropriate amount of glucose may be readily designed by those skilled in the art.

Likewise, any known method may be used to determine if an excess of glucose is present. Typically, an excess of glucose will result in increased synthesis of lactic acid and an increase in the concentration of hydrogen ions. Tissue acidosis can damage cells and induce lysosomal instability, activate lysomal enzymes and alter mitochondrial properties. Thus, any assay which would indicate the presence of any of these effects may be used to identify an excess of glucose.

Perhaps the simplest method of determining whether glucose is present in an amount sufficient to maintain the metabolic function of the cells but insufficient to cause acidosis is to prepare a series of solutions which differ only in their glucose content within the limits set

TABLE 1

| | COLLINS-2 FLUSH | SACKS-2 FLUSH | BELZER PERFUSATE | UW-1 FLUSH | BRETAN |
|---|---|---|---|---|---|
| COMPOSITION OF DIFFERENT INTRACELLULAR RENEWAL FLUSH SOLUTIONS (g/l) | | | | | |
| $KH_2PO_4$ | 2.0 | 4.16 | 3.4 | 3.4 | 1.54–2.56 |
| $K_2HPO_4.3H_2O$ | 9.70 | 9.70 | — | — | 7.38–12.2 |
| KCl | 1.12 | — | — | — | 0.84–1.40 |
| $KHCO_3$ | — | 2.30 | — | — | 0–2.87 |
| Mannitol | — | 37.5 | — | — | 20–37 |
| Glucose | 25 | — | 1.5 | — | — |
| $MgSO_4.7H_2O$ | 7.38 | — | 8 | 1.2 | 0–4.62 |
| $MgCl_2$ | — | (2 meq/ml) | — | — | 0–.4 meq/ml |
| Adenosine | — | — | 1.3 | 1.34 | 0.75–1.25 |
| Sodium Glutathione | — | — | 17.5 | 0.92 | — |
| Albumin | — | — | 5.3 | — | — |
| $NaHCO_3$ | 0.84 | 1.26 | — | — | 0.63–1.05 |
| Allopurinol | — | — | 0.113 | 0.113 | 0–0.125 |
| Verapamil | — | — | — | — | 0–1.0 |
| $K^+$ Lactobionate | — | — | — | 39.8 | — |
| Raffinose | — | — | — | 17.8 | — |
| Hydroxyethyl Starch | — | — | — | 5— | — |
| Osmolality (mOsm/kg) | 320 | 430 | 300 | 320–330 | 255–425 |
| pH | 7.00 | 7.00 | 7.10 | 7.40 | 7.20–7.50 |

While the amount of glucose employed in the solutions of the present invention will vary somewhat depending upon the type of tissue being preserved and the composition of the base solution, typically the amount of glucose employed will be below about 1000 milligrams per liter and above about 20 milligrams per liter (between about 5.55 mM and about 0.17 mM of glucose). For liver tissue, the amount of glucose should forth above and then experimentally determine which glucose concentration provides the optimum cold storage time for a particular tissue type.

The preservation solutions may be prepared in any known manner. Typically, the ingredients are simply added to distilled or deionized water. Particular orders of addition may be preferred in certain circumstances.

For example, it may be preferred to delay adding any component which is not stable for long periods in an aqueous environment, such as, for example, magnesium ions, reduced glutathione or certain antibiotics. In that case, all other ingredients may be mixed together, with the sensitive materials being added just prior to use of the solution. It should also be understood that the solution may be provided as a concentrate to be diluted with distilled or deionized water just prior to use.

A list of the ingredients of the preferred preservation buffer solutions is presented in Table 2. A range for the amount of each ingredient in the preferred solutions as well as the exact formulation of the most preferred solution are also provided. The most preferred solution is hereinafter referred to as "V-7 solution".

Special features of this most preferred, V-7 solution are that it:

1) is hyperosmolar as compared to extracellular fluid;
2) is high in its potassium content, approximating an intracellular potassium content;
3) is devoid of calcium;
4) is rich in magnesium as compared to extra or intracellular fluid;
5) contains nonpermeable anions which are not found in any other cold storage solutions;
6) contains small amounts of ascorbic acid;
7) contains a number of acid generating substrates such as succinate, fructose and glucose;
8) contains important anions for general cell function such as chloride and bicarbonate;
9) is free of plasma expanders and other high molecular weight compounds;
10) contains complexing agents for iron and other heavy metal ions.

Slices kept in V-7 solution under the oxygen tension of ambient air at the temperature of melting ice (0° C.) maintain their ability to express full viability (when cultured at 37° C.) for at least three days and up to ten days. The time of maintenance is somewhat dependent on the tissue and is highest for kidney and lowest for heart.

TABLE 2

| V-7 SOLUTION | | |
|---|---|---|
| | Preferred Range | Most Preferred Composition |
| Gluconate (K salt) | 30–120 mM | 60 mM |
| Saccharate (K salt) | 30–120 mM | 60 mM |
| Potassium phosphate (monobasic) | 25–30 mM | 25 mM |
| Sodium succinate | 1–3 mM | 2 mM |
| Magnesium sulfate | 3–6 mM | 5 mM |
| Magnesium chloride | 1–3 mM | 2 mM |
| Potassium bicarbonate | 1–3 mM | 2 mM |
| Glucose | 2–4 mM | 2 mM |
| Frutose | 2–4 mM | 2 mM |
| Glutathione (reduced) | 3–6 mM | 6 mM |
| Ascorbic acid (K salt) | 2–10 mM | 5 mM |
| Adenosine | 3–5 mM | 5 mM |
| Antibiotics (gentamycin or penicillin) | | μmolar amounts |
| Deferoxamine mesylate | | μmolar amounts |
| pH | 7.3–7.5 | 7.4 |
| Osmolality | 320–360 | 340 |

While further process aspects of the invention will be described specifically with respect to the V-7 solution, it should be understood that any preservation solution in accordance with the invention may be employed.

The preservation solutions of this invention may be used to preserve a variety of types of tissue slices. The tissue slices may be prepared in any known manner and preferably range from about 150 to about 250 μm in thickness to allow for optimal nutrient and gas exchanges between the slice, media and atmosphere.

In the preferred tissue slice preparation method a mechanical precision cut tissue slicer having a motor-driven oscillating blade rapidly produces slices of nearly identical dimensions in a controlled environment with minimal tissue trauma. Fresh human tissue is placed in ice cold V-7 solution and cylindrical tissue cores are prepared by advancing a rotating sharpened metal tube with constant pressure into the tissue which is suitably positioned on a support on the table of a drill press. Following the preparation of several uniform cylindrical tissue cores, tissue slices of defined thicknesses are obtained by use of the mechanical slicer which operates while submerged under ice cold V-7 solution. Individual tissue cores are placed into a matching cylindrical plastic holder and are lightly compressed with a piston holding adjustable weights. The combination of the distance between an adjustable base plate on the bottom of the tissue holder and the weight of the piston above determines the thickness of the slices. Slices are produced by pulling the immobilized weighted tissue cylinder across the rapidly oscillating razor blade. The freshly sectioned slices are then swept away by a stream of V-7 solution and collected in a basket. Slices can be produced at a rate of one per second. Upon completion of the slicing process, slices are pooled in a flat plastic tray and then transferred to their final culture vessels. In a preferred embodiment multiple cores are cut simultaneously such that the highest rate of slice production is achieved.

A common problem with conventional static organ culture techniques is degeneration of cultured slices at the slice-media interface or in the center of the slice. In the preferred culture system of the invention, however, both the upper and lower surfaces of the cultured tissue are exposed alternatively to the gas and liquid phase during the course of incubation. This is different from the method described by Smith et al. and can only be achieved with the slices affixed to the screens. The slices are affixed to the screens by applying a carrier in the form of a thin film of a non-toxic natural or synthetic material which is permeable to gas and the culture medium. Suitable film-forming materials include agarose and gelatin. In a preferred embodiment, individual tissue slices are floated from a tray containing a 0.5% agarose in a balanced salt solution at 37° C. into small stainless steel mesh half cylinders. These half cylinders are rolled from rectangular pieces of stainless steel screen and are held in teflon/silicone rubber cradles. Following the loading of a slice, the cradle is removed from the loading tray, blotted and cooled to produce a thin agarose gel film around the slice and screen which solidly anchors the slice onto the screen. Cradles with the slices affixed to the screen are then immersed into V-7 solution and sent to outside laboratories where any desired testing may be conducted on the slices. Alternatively, the cradles may be placed horizontally onto a temperature controlled vial rotator and cultured in a culture medium such that every time the cradle rotates it will dip the affixed slice through the surface of the culture medium, thus exposing both sides of the slice to the media and gas phase. Suitable rates of rotation are between about 1 and about 4 revolutions per minute. The preferred culture medium is a modified V-7 solution, particularly a V-7 solution in which the majority of the potassium ions are replaced by sodium ions. Most preferably, between about 85 and about 95% of the potassium ions present in the V-7 solution are replaced by sodium ions.

Several experimental protocols for determining slice viability or metabolism are known to those skilled in the art, including slice $K^+$ content, protein synthesis assays (for example wherein the incorporation of $^3$H-leucine in precipitated proteins is measured), lactate dehydrogenase leakage (diagnostic kit available from Sigma Chemical Co., St. Louis, Mo.), total protein measurement (diagnostic kit available from Pierce Chemical Co., Rockford, Ill.). and xenobiotics metabolism measurement (see Wishnies et al. (1991), Cryobiology, 28:216–226). The particular protocol selected is a matter of convenience.

In the examples that follow, $K^+$ content of the slices was determined as follows: slices were removed from the scintillation vials, blotted, weighed, and placed into 1 ml of distilled water. Slices were then homogenized by sonication with a cell disrupter at an intermediate setting (Model 350, Branson Sonic Power Co., Danbury, Conn.). The homogenate was centrifuged after the addition of 20 µl of 70% perchloric acid and the supernatant fraction assayed for $K^+$ by flame photometry (Model CA-51 Perkin Elmer, Danbury, Conn.). Results are expressed as µmoles $K^+$/g slice wet weight or as percent of control. See Fisher et al., In Vitro Toxicology 3:181-194) (1990). $K^+$ content of viable cells vary depending upon the particular type of tissue involved. Typically, the $K^+$ content of viable tissue varies from about 50 to about 80 µmoles per gram of slice wet weight. A decrease in the $K^+$ content indicates that cellular function is ceasing and the tissue is losing viability. The percentage of $K^+$ lost generally reflects the degree of which cell function has ceased and the tissue has died.

EXAMPLE 1 (COMPARATIVE)

Slices from three human livers were placed in a known preservation solution of the type described by Belzer and commonly referred to as "U.W. solution" and maintained at 0° C. The composition of the U. W. solution is given in Table I above. The $K^+$ content of the slices was measured at various intervals as a measure of the viability of the tissue. The results are shown in Table 3.

EXAMPLE 2

The solution used in Example 2 was the same as the U. W. solution of Example 1, with the exception that 360 mg/L of glucose was added to the solution. Again, slices from the three human livers were placed in the glucose-modified U. W. solution and stored at 0° C. The results are shown in Table 3.

EXAMPLE 3

Slices from three human livers were placed in V-7 solution (See Table 2) and stored at 0° C. The results are given in Table 3.

The results for Examples 1–3 are given in Table 3 as an average of the values obtained plus or minus the standard error of the mean. The experiment was started at 0 time, viability measured at that point and compared with several solutions for various periods of time. The results of Examples 1 and 2 clearly demonstrate that the addition of a limited amount of glucose to known preservation solutions increases the duration of viability of the tissue slice. A comparison of the $K^+$ content of the slices between 48 and 96 hours shows a significant increase in viability is provided by an amount of glucose sufficient to maintain the metabolic functions of the tissue cells but insufficient to stimulate acidosis.

TABLE 3

| Hours | EXAMPLE 1 U.W. SOLUTION | EXAMPLE 2 U.W. + GLUCOSE | EXAMPLE 3 V-7 |
|---|---|---|---|
| 0 | 66.7 ± 2.8 | 66.7 ± 2.8 | 66.7 ± 2.8 |
| 24 | 45.8 ± 1.5 | 46.3 ± 1.0 | 65.0 ± 2.1 |
| 48 | 33.7 ± 2.1 | 44.1 ± 1.7 | 63.2 ± 1.8 |
| 72 | 30.8 ± 2.7 | 42.8 ± 1.8 | 63.7 ± 1.5 |
| 96 | 30.1 ± 1.3 | 40.1 ± 2.1 | 62.9 ± 2.1 |
| 120 | 30.0 ± 1.0 | 35.7 ± 2.5 | 64.6 ± 2.5 |

EXAMPLES 4–9

A series of preservation solutions having a range of glucose contents were prepared based on the above-described V-7 solution. The composition of each solution is given in Table 4. Slices of human liver were placed into contact with each solution and maintained at 0° C. for ten days. The viability of the cells were then determined by measuring slice $K^+$ content. The results are given in Table 4. The $K^+$ content of a human liver slice at time zero is given in Table 4 as a control.

TABLE 4

| Example Number | Solution Composition | $K^+$ Content (µmoles $K^+$/gm) |
|---|---|---|
| Control | Fresh Slices | 61.7 |
| 4 | V-7 without glucose | 36.7 |
| 5 | V-7 with 1.0 mM glucose | 44.0 |
| 6 | V-7 with 2.0 mM glucose | 59.8 |
| 7 | V-7 with 4.0 mM glucose | 60.4 |
| 8 | V-7 with 5.0 mM glucose | 43.1 |
| 9 | V-7 with 6.0 mM glucose | 32.7 |

The data presented in Table 4 show that for a preservation buffer solution having the composition of V-7, a glucose content of between about 2 and about 4 mM is optimal. V-7 without glucose was unacceptable since the amount of glucose present (i.e., none) was clearly insufficient to maintain the metabolic functions of the cells. V-7 with 6.0 mM glucose was also unsatisfactory since 6.0 mM glucose clearly exceeded the amount required to maintain the metabolic functions of the cell and resulted in acidosis within the cell. The appropriate optimal glucose content for other preservation solutions and tissues can likewise be determined in this manner.

The preservation solutions of the present invention may also be used in cryopreservation of tissue by adding a cryoprotectant to the V-7 solution. Any known cryoprotectant can be employed. Suitable cryoprotectants include but are not limited to, dimethyl sulfoxide, glycerol, ethylene glycol and propanediol. While the amount of cryoprotectant added will depend upon the particular cryoprotectant chosen, typically between about 5% and about 50% may be added to the cold preservation solution employed.

In accordance with the cryopreservation method of this invention, tissue slices are contacted with a mixture of V-7 solution and a cryoprotectant and then cryopreserved by first cooling at a controlled rate, and then submerging the samples in a cryogenic fluid. The particular rate of cooling will depend upon the type of tissue being cryopreserved. For example, for human liver slices, a cooling rate in the range 0.25° to 1.0° C./min.

may be used, while for kidney slices a rate in the range 10° to 15° C./min. may be used. Liquid nitrogen is the preferred cryogenic fluid.

In one preferred embodiment of the cryopreservation method of the present invention, tissue slices are placed into a mixture of V-7 solution and dimethyl sulfoxide ("DMSO"). Preferably, the V-7 solution is modified by adding between about 8% and about 15% DMSO. The slices are maintained in the solution for 15-20 minutes at 0°-20° C. and then cooled at rates between about 0.25° and 1.0° C. per minute to −70° C. The slices are then rapidly immersed into liquid nitrogen at −196° C. The slices can be kept in this condition for a period of time which can range from months to years.

When there is a demand for the tissue slices, they may be retrieved and warmed. In a preferred embodiment the slices are warmed to between −150° and −100° C. by placing them into the gaseous phase of liquid nitrogen for approximately 2-5 minutes. Then the temperature is raised to −70° to −50° C. for another 2-5 minutes. The slices are then quickly thawed by immersing the slices in a large volume of 35°-39° C. V-7 solution. At that point slices may be reconditioned by culturing them at 37° C. in dynamic organ culture using fetal bovine serum as the reconditioning fluid or alternatively using a V-7 solution in which 85-95% of the potassium ions are replaced by sodium ions. This reconditioning fluid based on the V-7 solution may be prepared by substituting sodium salts in the amounts given in Table 2 above for the corresponding potassium salts contained in the V-7 solution. Preferably, the potassium salt of saccharate is still included in this reconditioning form of V-7 solution. After 2 to 24 hours in the reconditioning solution, the slices are ready for organ culturing which may be carried out in any commercially available culture medium, or the above-mentioned reconditioning fluids. The final culturing may be conducted at temperatures up to 38° C. for up to 72 hours.

In another embodiment of the cryopreservation methods of this invention, the tissue slices are placed in V-7 solution which has been modified by adding up to about 45% propylene glycol as the cryoprotectant. The careful introduction of these high concentrations of cryoprotectant is preferably done in a series of steps of 5-10% at 0° C. Slices are maintained at each concentration step for 3-5 minutes and then transferred to the next higher concentration. The exact number of steps will depend upon the final concentration of cryoprotectant to be used and the particular cryoprotectant employed. The overall cold equilibration with the cryoprotectant modified V-7 solution should normally not exceed 12 to 20 minutes. Slices may then be loaded into low mass plastic sieves and extremely rapidly cooled ($> -10000°$ C./minute) by vertical immersion of the carrier sieves into liquid nitrogen. The slices cryopreserved in this fashion should be translucent and glass-like and not white and snowy. There should also not be any white spots on the supercooled slices. Again the tissue is banked under liquid nitrogen in this state and kept there until needed. At that time the tissue may be thawed at extremely rapid rates ($> +10000°$ C./minute) in order not to pass through a stage in which ice crystals are formed. Properly thawed slices can be reconditioned as previously described and then reintroduced to V-7 solution for packaging and cold shipment.

As with any human tissue sample, a certain risk of contamination with a variety of tissue borne disease causing agents exists. The tissue slices may therefore be packaged in accordance with a further aspect of this invention in a manner to minimize the risk of infection. The slices are packaged in accordance with the invention such that they are enveloped in a suitable carrier and inserted into disposable dynamic organ culture vessels. The main risk for anyone working with this tissue would be direct blood contact as per a cut or prick with a sharp instrument or through an open wound. Packaging in accordance with the present invention limits exposure to the tissue by the researcher to the potential infectious agents borne by the tissue. The protection by the present packaging is mainly due to the absence of any requirement for sharp or pointed tools in the manipulation of such packaged slices. Risks from additional aerosol exposure and manual handling can be essentially excluded by proper handling precautions, such as for example double gloving, wearing aerosol masks, and eye protection and working inside a biosafety hood. Packaging of slices in disposable dynamic organ culture vessels can be achieved by using a special carrier material to affix the slices to a cradle. Suitable carrier materials include non-toxic natural or synthetic materials capable of forming a film which is permeable by both gas and the culture medium. Preferably, the carrier material is applied by introducing the carrier material to a balanced salt solution. Most preferably the carrier material will be liquid at 37° C. but will form gels at lower temperatures and will not melt if exposed once again to 37° C. Such carrier solutions include but are not limited to 0.5% agarose and 2% gelatin solutions. When tissue slices are loaded onto the cradles while submerged in warm (37° C.) balanced salt solution containing 0.5% agarose, blotted and cooled to lower temperatures (0°-10° C.), a thin gel film will surround and attach the slice to the screen. After slices are affixed to the screen, it requires vigorous shaking to remove them thus now making it possible to wash medium over the upper surface of the affixed slice during dynamic organ culture. The goal of alternatively exposing both upper and lower surfaces of the slice to either gas or media phase has now been accomplished. Affixing slices to the screens also helps in shipping cold preserved slices in V-7 to other laboratories.

Packaging tissue slices in the above manner also requires special shipping arrangements such that the dynamic organ culture vessels bearing the envelope with human tissue is at all times kept in a submerged position in V-7 solution. A special cold shipping container is contemplated in accordance with a further aspect of the invention. The shipping container of the present invention includes an inner container having a substantially spherical inner surface. The inner container may simply be a spherical container such as a plastic globe. The spherical container is placed into an outer receptacle. Preferably the outer receptacle is regular in shape so as to allow stacking thereof and includes a recess adapted to receive the spherical container. The outer container may advantageously be constructed as two halves each having a hemi-spherical recess. Alternatively, the outer container may have a cylindrical recess adapted to snugly receive the spherical container. Preferably, for use in connection with the transport of tissue slices, the outer container has insulating properties. To this end, the outer package may be molded from expandable polystyrene beads.

Within the inner container is a self-righting member. The self-righting member includes a riding surface which is substantially parallel to the inner surface of the inner container. A lubricating material is located between the riding surface of the self-righting member and the inner surface of the inner container. The lubricating material may be any liquid which allows the self-righting member to slide smoothly on the interior surface of the spherical container.

For cold shipping of tissue slices the self-righting member is preferably a hemi-spherical block of ice and the lubricating material is water which is either added to the container or produced by melting of the ice. The actual rack in which the tissue loaded dynamic organ culture vessels are held is anchored tightly to this half spherical ice block with appropriate anchors. This ice block and sample rack will always assume a horizontal orientation because the ice block will float on its own melted ice. This will allow the slices to be in the same relative orientation and exposed to the V-7 solution at all times. When this special shipping container is combined with slice affixment to the carrier screens in the organ culture vessel as described above, slices will be continuously exposed to V-7 cold preservation solution even when occasionally roughly handled during shipment.

What is claimed is:

1. A method for the cold preservation of organ tissue comprising storing said tissue in an aqueous preservation solution comprising:

1-5 mM glucose; 30-120 mM gluconate; 30-120 mM saccharate; 25-30 mM potassium phosphate(monobasic); 1-3 mM sodium succinate; 3-6 mM magnesium sulfate; 1-3 mM magnesium chloride; 1-3 mM potassium bicarbonate; 2-4 mM fructose; 3-6 mM glutathione; 2-10 mM ascorbic acid; 3-5 mM adenosine and micromolar amounts of deferoxamine mesylate and gentamicin or penicillin.

2. The method of 1 wherein the solution further comprises a cryoprotectant and the method further comprises immersing the preserved tissue into a crygenic fluid.

3. The method of claim 2 wherein said cryoprotectant is selected from the group consisting of dimethyl sulfoxide, glycerol, ethylene glycol and propanediol.

4. The method of claim 2 further comprising the step of cooling the tissue at a controlled rate prior to immersing the tissue in the cryogenic fluid.

5. The method of claim 2 wherein said cryoprotectant comprises from about 5% to about 50% by weight of said solution.

6. The method of claim 2 wherein said storing step comprises sequentially placing the tissue in a series of solutions, each solution in the sequence having a greater concentration of cryoprotectant than the previous solution.

7. The method of claim 2 further comprising the step of thawing the cryopreserved human tissue slices.

* * * * *

UNITED STATES PATENT AND TRADEMARK OFFICE
CERTIFICATE OF CORRECTION

PATENT NO. : 5,328,821

DATED : July 12, 1994

INVENTOR(S) : Robyn L. Fisher et al.

It is certified that error appears in the above-identified patent and that said Letters Patent is hereby corrected as shown below:

Column 14:
In claim 2 at line 3, "crygenic" should read --cryogenic--.

Claims 8 and 9 should be added as follows:

--8.   The method of claim 7 wherein the cryogenic comprises liquid nitrogen and said thawing step comprises:

warming the tissue to between about -150°C and about -100°C by raising the tissue out of the liquid nitrogen and into the gas phase above the liquid nitrogen;

warming the tissue slices to between about -70°C and about -50°C by raising the tissue further above the liquid nitrogen and higher into the gas phase; and warming the tissue slices to 37°C by immersing the slices into a large volume of said preservation solution which has been heated to 37°C.

UNITED STATES PATENT AND TRADEMARK OFFICE
CERTIFICATE OF CORRECTION

PATENT NO. : 5,328,821
DATED : July 12, 1994
INVENTOR(S) : Robyn L. Fisher, et al.

It is certified that error appears in the above-indentified patent and that said Letters Patent is hereby corrected as shown below:

9.   A method as in claim 8, further comprising the step of contacting the tissue with a final culturing medium at a temperature of up to 38°C for up to 72 hours, the final culture medium being selected from the group consisting of fetal calf serum or said preservation buffer solution.--

Signed and Sealed this

First Day of November, 1994

*Attest:*

BRUCE LEHMAN

*Attesting Officer*     *Commissioner of Patents and Trademarks*